United States Patent [19]

Zomer

[11] Patent Number: 5,235,989
[45] Date of Patent: Aug. 17, 1993

[54] APPARATUS FOR SENSING RESPIRATION MOVEMENTS

[75] Inventor: Jacob Zomer, Haifa, Israel

[73] Assignee: Sleep Disorders Center, Haifa, Israel

[21] Appl. No.: 759,108

[22] Filed: Sep. 6, 1991

Related U.S. Application Data

[63] Continuation-in-part of Ser. No. 566,177, Aug. 10, 1990, abandoned.

[30] Foreign Application Priority Data

Mar. 7, 1990 [IL] Israel .................................. 093675

[51] Int. Cl.⁵ .............................................. A61B 5/08
[52] U.S. Cl. .................................... 128/721; 128/774
[58] Field of Search ............... 128/716, 721, 722, 774

[56] References Cited

U.S. PATENT DOCUMENTS

| | | | |
|---|---|---|---|
| 2,614,144 | 10/1992 | Howatt | 128/721 |
| 4,576,179 | 3/1986 | Manus et al. | 128/721 |
| 4,602,643 | 7/1987 | Dietz | 128/721 |

FOREIGN PATENT DOCUMENTS

| | | | |
|---|---|---|---|
| 1492875 | 3/1975 | United Kingdom | 128/721 |
| 2181555 | 3/1988 | United Kingdom | 128/721 |

*Primary Examiner*—Kyle L. Howell
*Assistant Examiner*—Robert L. Nasser, Jr.
*Attorney, Agent, or Firm*—Morgan & Finnegan

[57] ABSTRACT

An apparatus for accurately indicating respiration movements on a recorder. The apparatus comprises two piezoelectric transducers which are disposed parallel to each other and each mounted on a support member. Between the two transducers is an elastic belt forming an elastic band, a portion of the belt having a loop or wave shape. The entire apparatus is enclosed in a rigid housing, and the elastic band wraps around the patient. When horizontal stretching forces are applied to the band, i.e. during respiration, the loop shape of the belt causes both piezoelectric transducers to bend in the same direction and generate an electronic signal for recording. Any other external force will cause the two transducers to bend in opposite directions, thereby canceling each other, and generating no signal for recording. The apparatus may further be used for prolonged periods of time and is also very sensitive, thereby resulting in accurate respiration data.

24 Claims, 6 Drawing Sheets

APPARATUS FOR SENSING RESPIRATION MOVEMENTS

This Application is a Continuation-In-Part of Ser. No. 07/566,177 filed on Aug. 10, 1990 and now abandoned.

BACKGROUND AND OBJECTS OF THE INVENTION

The present invention relates generally to a apparatus for determining respiration movements, and, more particularly, to an apparatus for accurately determining respiration movements without interference from external forces.

Determining respiration movements is important in patient health care and biophysical research. For example, monitoring a patient's respiration allows an early alarm to be sounded when the patient has trouble breathing or when breathing stops. Further, monitoring respiration is beneficial in researching many sleep disorders, for example apnea, which interfere with proper respiration.

There are various known devices for respiration monitoring. One well-known device comprises a rubber tube which is filled with mercury or a saline solution, and which is closed at the two ends. The tube is fitted around the chest of a patient, and the respiration movements are measured by determining the voltage generated across the tube when a fixed current is passed through the tube. The contents of the tube act as a variable resistor, the resistance of which changes as the tube is stretched or contracted by the patient's respiration movements. A similar device was later developed in which a tube contained a solid substance such as graphite powder instead of a liquid. The main disadvantage of these devices, however, is that the voltages generated in response to the patient's respiration movements is inaccurate because the generated voltage includes voltage due to not only respiration movement but also voltage caused by various non-respiratory movements upon the tube. Furthermore, the elastic tube sometimes ruptures, leaking the liquid or powder upon the patient, and causing further inaccurate results from the signal obtained. Another group of devices for measuring respiration movements is based on two small electrodes which can be taped onto the chest of the patient. While the electrodes are in contact with the patient's skin, an electric current is passed between the two electrodes. A varying voltage is then detected, which varies with the respiration movements of the patient. The variance is caused by the varying resistance of the chest wall itself. The chief disadvantage of devices employing taped electrodes is the requirement of a direct contact with the patient's skin, which necessitates the prior removal of the subject's clothes, which in an emergency or casualty situation is actually impossible. Further, there is an increased danger of electrocution.

A later device was developed which did not require direct skin contact, but which could be attached outside the clothing. According to this device, as described in U.S. Pat. No. 2,181,555, a piezoelectric transducer is mounted on a flexible support upon which the transducer can be bent in response to the displacement of a patient's chest during respiration movements, thereby generating an electrical signal. The main disadvantage of this device is that during respiration movements the entire device, flexible support and transducer, stretches and deforms, assuming a concave shape which matches the shape of the body. Thus, the electrical signals generated and recorded from this deformed device do not truly represent respiration movements but are instead the result of the deformation of the transducer. Furthermore, where an external perpendicular stress, not related to respiration, is applied, the signals are inaccurate. This might occur, for example, while a person is moving while sleeping on a solid object or member, e.g. their own hand.

Another device is described in PCT Patent Application AU 85/00163. The device comprises a sensor with a flexible member and an elongated rigid member disposed thereon. A piezoelectric transducer is disposed upon one end of the rigid member. The disadvantage of this device is, as before, that the sensor will register non-respiratory external stresses in addition to the respiration movements.

The above brief review shows a long felt need for an improved apparatus which will accurately indicate a patient's respiration movements and will not be influenced by other external factors.

It is an object of the present invention to provide a simple apparatus for obtaining a true indication of repsiration movements.

It is a further object of the present invention to provide a simple apparatus which indicates only the respiration movements and which also does not require direct contact with the skin.

It is yet another object of the present invention to provide a simple apparatus which is capable of sensing accurately the respiration movements of a patient and reduce or nullify the influence of artifacts due to bending or pressing forces other than stretching forces that are applied by the respiration movements.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the invention consists of an apparatus for accurately indicating respiration movements on a recorder, which preferably comprises two piezoelectric transducers mounted on a support member, where the transducers are disposed opposite and parallel to one another, and an elastic belt having at least one portion thereof being disposed in a loop-like or wave shape which extends angularly outwardly from the unlooped portion of the belt at least 5° in alternative directions, where the belt material may be stretched at its two ends to form a flexible band, which surrounds a patient's chest atop the patient's clothing, whereupon stretching of the band by the patient's respiration movements causes the two piezoelectric transducers to generate a proportional electrical signal. The signal is then transmitted to a recorder. The signal input may be recorded on an electroencephalograph, strip chart, or any other known instrument such as used in sports activities. Further, the structure described effectively eliminates false signals caused by external forces other than respiration movements.

According to one embodiment of the present invention, the belt is located between the two parallel piezoelectric transducers.

According to another embodiment, the belt is disposed substantially parallel to one of the transducers, but is not located between the two transducers as in the first embodiment. As above, upon respiration movements of the patient, the elastic band stretches, causing at least one piezoelectric transducer to generate a proportional electrical signal, which is transmitted to a recorder.

The elastic belt has an attachment mechanism connecting the two ends, for example an adhesive or a fastener.

According to a most preferred embodiment, the entire device is located in a rigid housing, with the entire enclosed space filled with a resilient constituent, for example elastic glue or any type of silicone glue.

The electrical output from the two piezoelectric transducers is fed to a low-pass filter from which it is then transferred to a voltage divider, producing a desired output signal range. This signal is supplied to a cable leading to a pair of plug-type connectors linked to a recorder, which records the signal.

It will be appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part hereof, illustrate preferred embodiments of the invention and, together with the detailed description, serve to explain the principles of the invention.

BRIEF DESCRIPTION OF THE DRAWINGS

The invention will be more fully understood and other features and advantages thereof will become apparent from the description given below of an exemplary embodiment of the invention, in which.

DETAILED DESCRIPTION OF PREFERRED EMBODIMENTS

Figure 1:
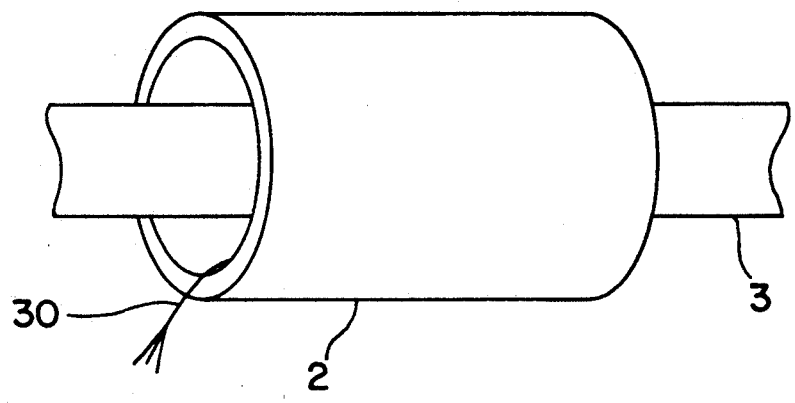
FIG. 1 is a top view of a respiration sensing apparatus of the present invention.

Referring now to the accompanying drawings, wherein like reference characters refers to like parts throughout the various views, there are shown in FIGS. 1-11 the preferred embodiments of the respiration sensing apparatus according to the present invention.

FIG. 1 shows a tube-shaped housing 2 having an opening at both ends. Housing 2 is made of a rigid material, for example hard rubber, aluminum, or other rigid material. As will become readily apparent to one skilled in the art, other materials may also provide the requisite rigidity. Although the protective housing is rigid, housing 2 nonetheless remains susceptible to pressures from external forces, for example a patient pressing on the apparatus with their hand.

Figure 11:
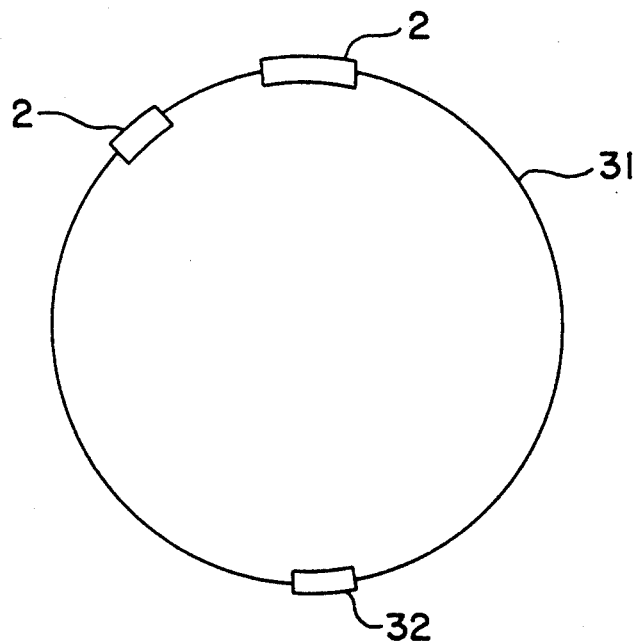
FIG. 11, is a view showing the apparatus of the present invention with the band and fastener.

As shown in FIGS. 1 and 11, a belt 3 passes through the housing 2, and forms a band 31 surrounding the torso of the patient, particularly, the chest cavity. The belt 3 is made of a thin pliable sheet or membrane. Typical materials for the belt 3 include many common elastic plastics, such as polyvinyl chloride (PVC), polyethylene, or polyamide. Also shown in FIG. 1 is a wire cable 30 from the interior portion of the housing 2.

Figure 2:
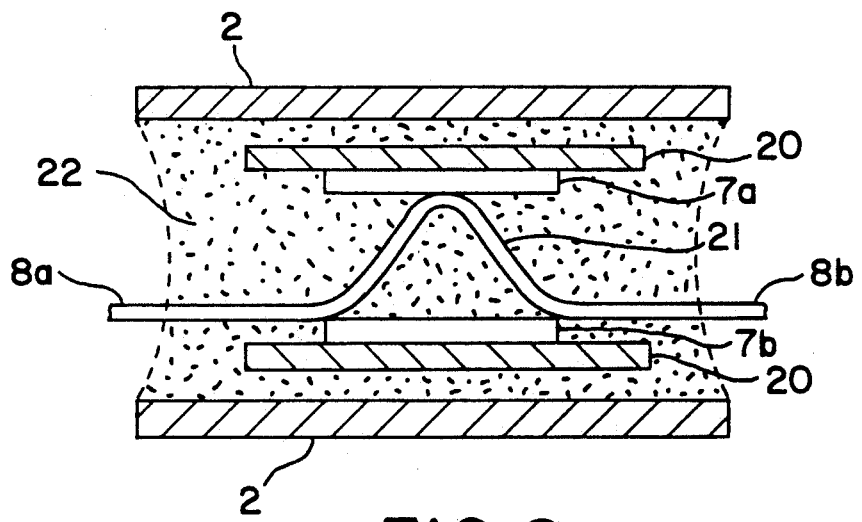
FIG. 2 is a cross-sectional view of the housing of an embodiment of the respiration sensing apparatus of the present invention showing a belt having a portion thereof disposed in a loop-like or wave shape situated between two piezoelectric transducers, with no tensional forces on the belt or pressure on the transducers.
Figure 8A:
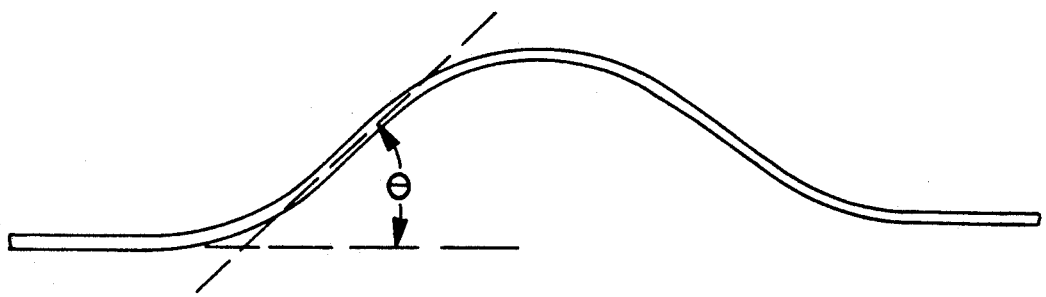
FIGS. 8A and 8B are side views of various loops or wave shapes for the belt, showing the angle of the wave.
Figure 8B:

FIG. 2 is a side cross-sectional view of the housing 2 as shown in FIG. 1, showing two piezoelectric transducers, 7a and 7b, which are disposed opposite and parallel to one another within the housing. Each transducer is mounted to a support member 20, which is preferably attached to the side wall of the housing 2. Although attached to the rigid housing, the support member is preferably flexible and may bend to form either a convex or concave shape. Support member 20 is preferably a flexible metal sheet. In between the two transducers is the belt 3, which has one or more loops 21, resembling an inverted U configuration. As shown in FIGS. 8A and 8B, loop angle Θ, which extends angularly outwardly from the unlooped portion of the belt, is at least 5°, and is preferably 20°. Although the preferred loop shape is curved, the "loop" may instead form a point, resembling a sawtooth or inverted V-shape configuration, as shown in FIG. 8B. The loop shape 21 of the belt 3 is stiffened by treatment with glue or other hardening compounds to maintain the loop shape and keep the loop from flattening out. This stiffened loop shape 21 is substantially maintained even when the band 31 tightens, pulling at the sides of the stiffened loop. The loop 21 may contact both piezoelectric transducers: the rise and fall areas touching the lower transducer 7b and the crest of the loop or wave shape touching the upper transducer 7a. However, as will become readily apparent to those skilled in the art, physical contact between the loop 21 and the transducers is not necessary.

The non-glued portions of the belt 3 (band 31) remain elastic and subject to stretching. The band 31, as shown in FIG. 11, extends around the patient's torso, and may be connected by a clasp, adhesive tape, Velcro ®, or any other fastening mechanism 32, which would be readily apparent to one skilled in the art. The two ends, 8a and 8b, on either side of the stiffened loop 21, shown in FIG. 2, form part of this band. FIG. 11 also shows that multiple housings 2 may be attached to the band 31.

Enclosed in the interior portion of the rigid housing 2 shown in FIG. 2 is a resilient constituent 22, for example silicone rubber or elastic glue, which constrains the movement of the elements within, for example the stiffened loop 21 of the belt 3. This resilient constituent 22 fills the empty spaces within the housing 2, particularly those spaces both above and below the stiffened loop 21.

Figure 3:
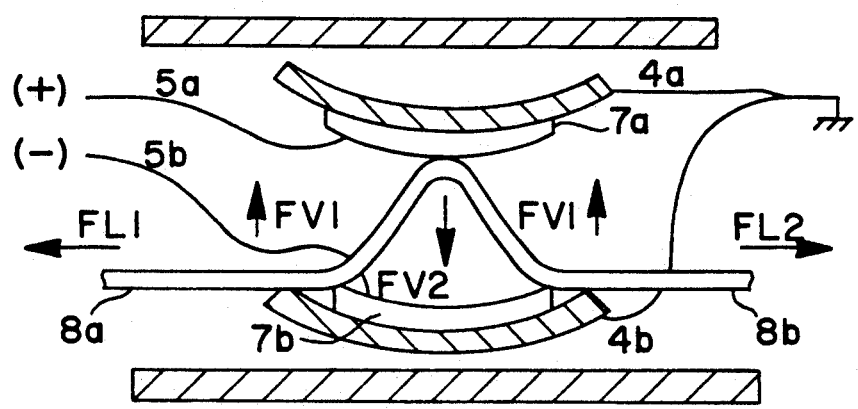
FIG. 3 is a cross-sectional view of the respiration sensing apparatus of the present invention as in FIG. 2 showing longitudinal tensional forces along the ends of the belt and pressure against the piezoelectric transducers.

During respiration, the patient's chest cavity expands and the elastic band 31 surrounding the patient's chest stretches. The stretching due to respiration movement shown in FIG. 3 creates two longitudinal forces, FL1 and FL2, pulling the two ends 8a and 8b of the belt 3, which in turn pull on the stiffened loop 21, which is surrounded by the resilient constituent 22 (not shown). Since the loop 21 has been treated with glue or some other hardening agent, the now stiffened loop shape is no longer elastic to stretching, but is nonetheless responsive to bending forces. Thus, longitudinal tensional forces due to stretching are transformed into perpendicular forces FV1 and FV2, which cause the piezoelectric transducers 7a and 7b and support members 20 to bend. More particularly, the vertical force FV2 from the stiffened loop 21 presses against the resilient constituent 22 under the loop, which in turn presses against the piezoelectric transducer 7b and support member 20 causing both to bend and form the convex shape as shown in FIG. 3. Concurrently, the vertical forces FV1 on either side of the stiffened loop 21 press in the opposite direction. The FV1 forces act on the resilient constituent 22 on either side of the stiffened loop 21, which presses on the two ends of the piezoelectric transducer 7b and support member 20, causing both to bend and form a convex shape also.

As will become readily apparent to those skilled in the art, an alternative embodiment has a similar structure but does not include the resilient material 22. The interior portion may instead be filled with air or another nonresilient substance. The stiffened loop 21 in this embodiment is attached to piezoelectric transducer 7a at the apex or crest of the loop. The longitudinal forces FL1 and FL2 pull the loop 21 downwards, with the transducer 7a and support member 20, forming a convex shape as above.

Piezoelectric materials by their nature transform mechanical forces or stresses upon the crystalline latticework into electrical voltage. In the present invention, the particular stresses and bends placed upon the piezoelectric transducers 7a and 7b are likewise converted into electrical voltages. FIG. 3 shows various electrical leads attached to the piezoelectric transducers 7a and 7b and support member 20. Two electrical leads 4a and 4b are attached to the support member 20, which acts as a shield. An electrical lead 5a is attached to the piezoelectric transducer 7a, and an electrical lead 5b is attached to transducer 7b. As shown in FIG. 3, the bending stress placed on the piezoelectric transducer 7a produces a voltage on the surface of the piezoelectric transducer 7a. An opposite voltage is produced on the opposite surface of the piezoelectric transducer 7a, which contacts the support member 20 attached to transducer 7a. Similarly, the other bending forces cause piezoelectric transducer 7b to produce a voltage, but transducer 7b is aligned to produce an opposite voltage when bent into a convex shape. The electrical leads 4a and 4b are attached to the support member 20, which acts as a shield.

Thus, two longitudinal forces FL1 and FL2 upon the band 31 stretch the band (belt 3) upon each expansion of a patient's chest during respiration movements, and as a result of these forces, the two piezoelectric transducers bend in the same convex manner. The voltages resulting from this convex transducer bending are sent along the electrical leads 5a and 5b attached to the piezoelectric transducer surfaces to a differential subtractor, which subtracts the two voltages. In FIG. 3, the voltage from piezoelectric transducer 7a as applied to electrical lead 5a is opposite to the voltage from transducer 7b on lead 5b. Differential subtraction of the two opposing voltages adds the two voltages, thereby generating and transmitting a signal representing one respiration movement, which is then passed to a recorder. As will be noted below, this differential construction suppresses stresses caused by any non-respiration movements.

Figure 4:
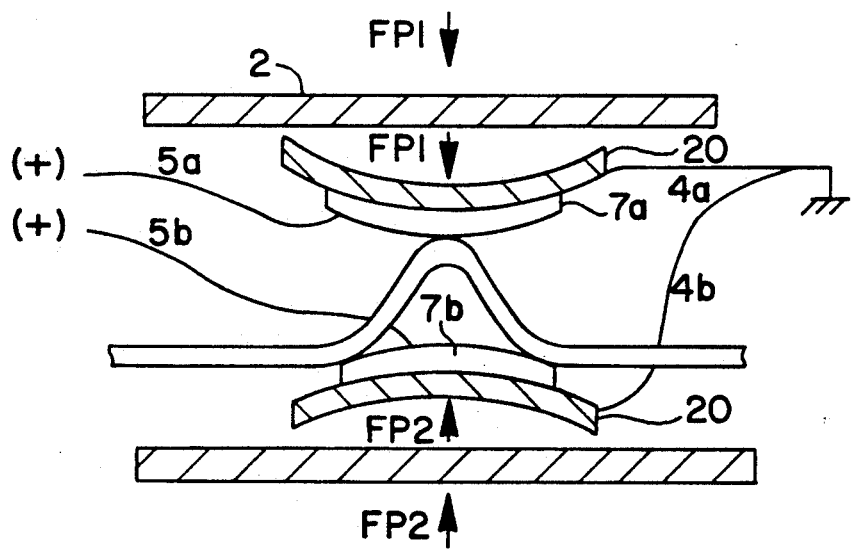
FIG. 4 is a cross-sectional view of the respiration sensing apparatus of the present invention as in FIG. 2 showing external perpendicular forces against the housing, bending the transducers.

In FIG. 4, two perpendicular forces FP1 and FP2 are shown. The perpendicular forces are of the type caused by external non-respiration movements, for example pressing against the housing 2 or other external contacts. When an external non-respiratory force FP1 acts on the apparatus of the present invention, an equal and opposite reactive force FP2 is generated. The perpendicular force FP1 presses against the resilient material 22 between the housing wall 2 and the support member 20. The resilient material 22 presses against the support member 20, which is attached to piezoelectric transducer 7a, and both bend to form a convex shape. As in FIG. 3, this convex bending generates a voltage on the surface of piezoelectric transducer 7a and on the lead 5a. However, unlike FIG. 3 the other support member 30 and transducer 7b are bent concave by the perpendicular force FP2, which generates an equal voltage on the surface of piezoelectric transducer 7b and lead 5b.

Since these external perpendicular forces are not due to respiration movements, the voltages generated by these contacts should not produce a signal indicating a respiration movement. The voltages caused by undesirable external perpendicular forces are sent to the differential subtractor, which as before subtracts the two voltages. Here, however, the voltages are the same, and the voltages cancel in the subtraction. Thus, no signal indicating a respiration movement is produced. Thus, external perpendicular forces due to non-respiration movements, contacts, accelerations or other artifacts do not generate a signal to the recorder, allowing only those signals produced by the band stretching and convex bends as shown in FIG. 3.

In an embodiment without resilient material 22, the apex of the loop 22 is attached to transducer 7a. Upon application of the longitudinal forces, transducer 7a is bent to form a concave shape, thereby generating a voltage. Transducer 7b, however, is unaffected, and no voltage is generated. Differential addition nonetheless measures a respiration movement since the voltages do not cancel.

Figure 5:
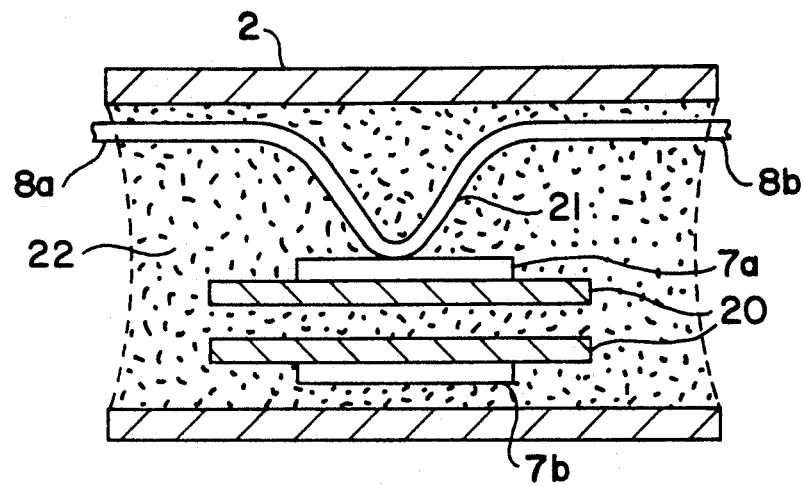
FIG. 5 is a cross-sectional view of the housing of a second embodiment of the respiration sensing apparatus of the present invention showing the belt and loop or wave shape positioned outside of the space between the two transducers, with no tensional forces on the belt or pressure on the transducers.

In FIG. 5, there is shown a second embodiment of the present invention where the belt 3 is not between the two piezoelectric transducers 7a and 7b, but is disposed above one of the transducers, for example 7a, with the apex of the loop 21 in the vicinity or contacting the outer surface of transducer 7a.

Figure 6:
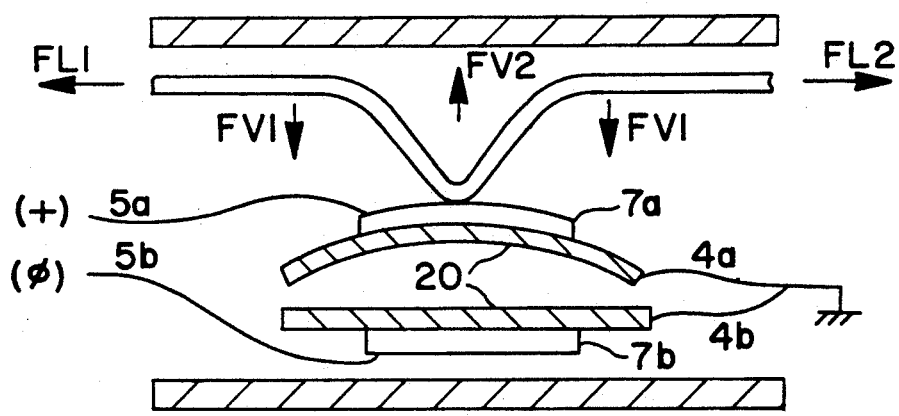
FIG. 6 is a cross-sectional view of an apparatus as in FIG. 5 showing longitudinal tensional forces along the ends of the belt and pressure against the piezoelectric transducers.
Figure 7:
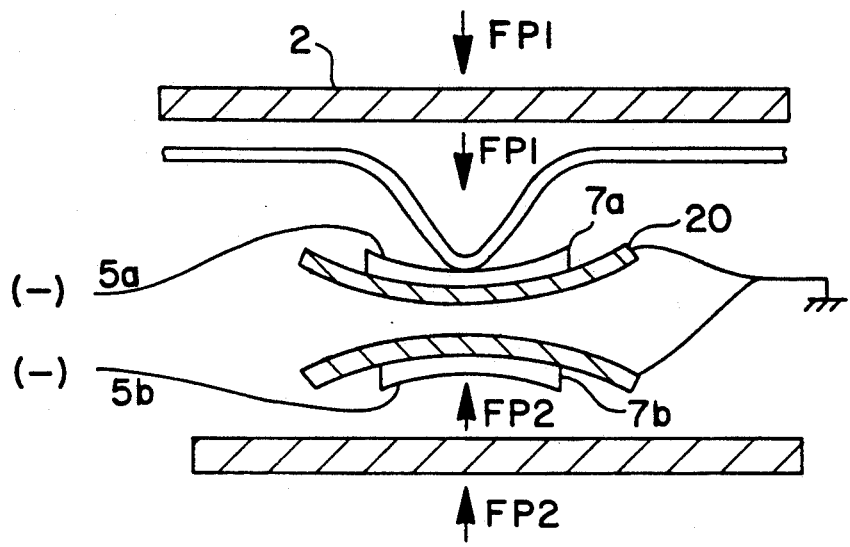
FIG. 7 is a cross-sectional view of an apparatus as in FIG. 6 showing perpendicular forces against the housing, bending the transducers.

FIG. 6 illustrates the effect on the second embodiment of the longitudinal forces FL1 and FL2 caused by the stretching of the band 31 during respiration movements. As with FIG. 3, longitudinal tensional forces FL1 and FL2 are transferred to the perpendicular vertical forces FV1 and FV2, with the vertical force FV2 pressing against the resilient constituent 22 under the loop 21 and FV1 pressing in the opposite direction on the resilient constituent 22 on either side of the loop 21. The perpendicular forces on the piezoelectric transducer 7a and its attached support member 20 cause both to bend and form a concave shape as shown in FIG. 6. The perpendicular forces FV1 and FV2, however, need not affect the lower transducer 7b. Thus, although a voltage is formed on the surface of piezoelectric transducer 7a when the transducer 7a bends, no voltage is produced from piezoelectric transducer 7b when transducer 7b bends. Differential substraction of the voltages in FIG. 6, results in a new voltage since the voltages do not cancel, and a respiration movement signal is then sent to the recorder. In FIG. 7, however, the two voltages on the two transducers are the same, and differential substraction cancels them. Thus, no respiration movement signal is produced.

In an embodiment without resilient material 22, the wave shape 22 is attached to transducer 7a. Upon application of longitudinal forces, transducer 7a is bent to form a convex shape, thereby generating a voltage. Transducer 7b, however, is unaffected, and no voltage is generated. Differential subtraction nonetheless measures a respiration movement since the voltages do not cancel.

FIGS. 8A and 8B illustrate two types of loop or wave shapes 21 which may be employed in the present invention. The first is a curved wave shape, which resembles an inverted U-shaped configuration, and the second has a straight-edge wave shape, resembling a sawtooth or an inverted v-shaped configuration. As will become readily apparent to those skilled in the art, numerous other shapes can be used without departing from the scope of the claimed invention. Both the curved and straight-edged loop shapes 21 have an angle of steepness Θ extending angularly outward from the unlooped portion of the belt 3, where said angle is preferably 20°, but no less than 5°. The minimal angle is critical in order to achieve a differential effect, making the apparatus of the present invention sensitive to respiration movements but not sensitive to non-respiration movements, for example perpendicular stresses or accelerations. As noted, the loop or wave shapes are maintained by hardening the loop 21 in a glue or other hardening agent, which makes the loop inelastic to stretching but is nonetheless responsive to bending forces. Further, although only one loop is shown, a plurality of loops may be employed forming a series of loops or wave shapes.

Figure 9:
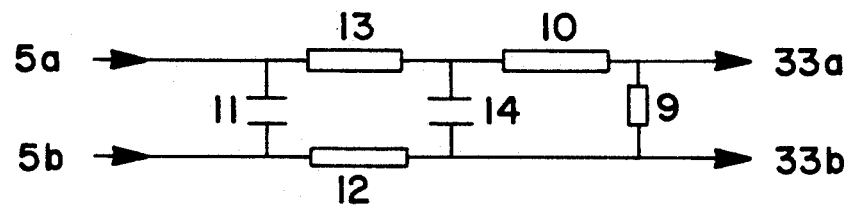
FIG. 9, is a scheme of the electric circuit which filters the outputs of the piezoelectric transducers.

A well-known problem with piezoelectric materials is their susceptibility to static. Thus, piezoelectric materials preferably use an output filter to avoid such noise. FIG. 9 shows a circuit diagram of a well-known filter which includes four resistors 9, 10, 12 and 13 connected to the piezoelectric transducers 7a and 7b through electric leads 5a and 5b, respectively. Generally, the resistors will be in a range of between 1 to 10 megaohms. Two capacitors 11 and 14 are attenuating high frequencies and thus will provide a clear electric signal to a recorder (not shown). Generally, the capacitators will be in the range of between 0.1 to 10.0 microfarads. The filter output wires 33a and 33b pass to a voltage divider (not shown), which produces an output signal within a desired output range. This signal is then applied to a cable leading to a pair of plug-type connectors linked to a recorder, which records the signals.

Figure 10A:
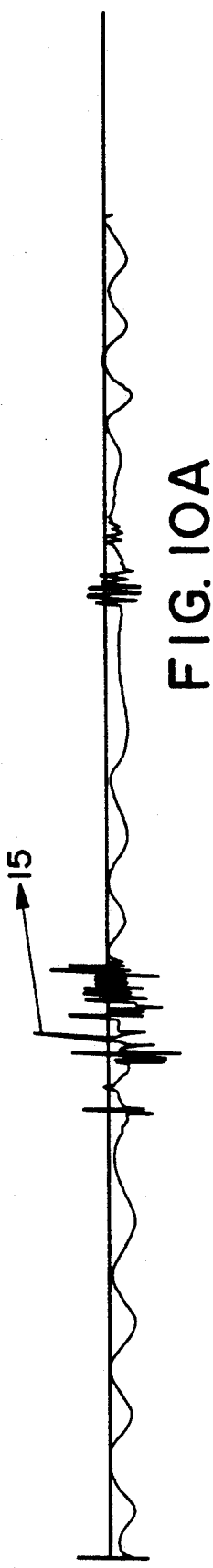
FIG. 10, shows three graphs which illustrate the curves of respiration signals recorded by a recorder connected to the output of the signal conditioning circuit, wherein only graph C is that of the apparatus according to the present invention, the other two graphs, A and B, being presented for comparison purposes.
Figure 10B:
Figure 10C:
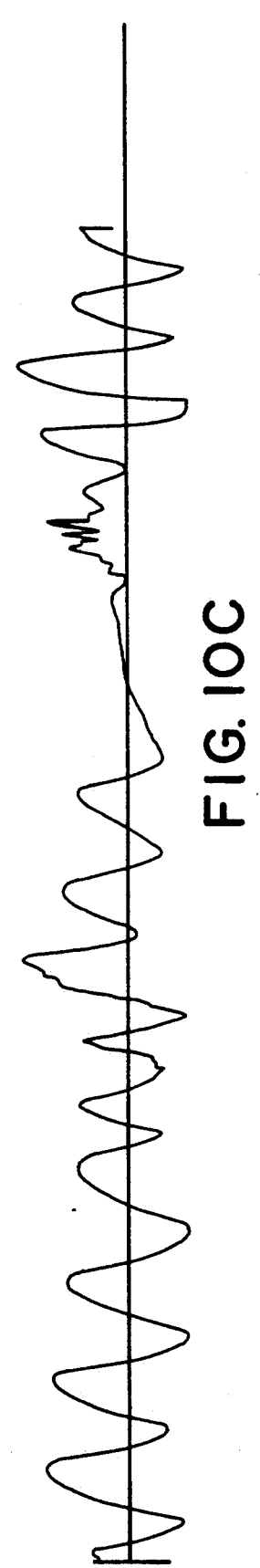

FIG. 10 shows three graphs of the curves of respiration movements of a subject person, as obtained on a recorder. Graph A illustrates the curve obtained with an apparatus comprising two piezoelectric transducers but without the belt 3 (for comparison purposes). Graph B illustrates the curve obtained with an apparatus comprising one piezoelectric transducer with the belt 3 possessing the specific wave shape (also for comparison purposes). Graph C illustrates the curve obtained with an apparatus according to the present invention.

Graphs A and B clearly show the artifacts regions 15 and 16 which are due to non-respiration movements. As clearly appears, only the device according to the present invention, as shown in Graph C, eliminates the above artifact regions, due to placing the belt 3 with the wave shape 21 between the two piezoelectric transducers 7a and 7b. Only this structure will eliminate the perpendicular external forces, and provide an accurate measurement of the respiration movements.

Among the advantages of an apparatus according to the present invention, in addition to its accurate measurement capabilities, is that it is not necessary to remove the patient's clothes since a firm contact between the device and the clothes on the chest area will be sufficient to obtain an accurate graph representation of the respiration movements. This firm contact may be achieved by connecting the ends of the band 31 by adhesive tape or any other fastening mechanism 32, shown generally in FIG. 11.

Another advantage of the present apparatus results from its rigid construction due to its mode of operation, which does not require the apparatus to bend even when the band 31 is applied onto a large circumference. In this manner it can be easily installed in a protective rigid housing 2, which will allow prolonged use of the apparatus. As will be realized, any bend of the belt will impart significant inaccuracies in the signal produced on the recorder.

The respiration sensing apparatus according to the present invention is both unencumbering to a person on which it is applied and although having extremely high sensitivity, it is of simple and inexpensive construction. Further, it is self-balancing and particularly easy to install and operate, providing highly accurate and useful respiration movement data.

While the invention has been described in connection with certain preferred embodiments it will be understood that it is not intended to limit the invention to those particular embodiments. On the contrary it is intended to cover all alternatives, modifications and equivalents as may be included in the appended claims.

Some specific components figures and types of materials are mentioned, but it is to be understood that such component values, dimensions and types of materials are, however, given as examples only and are not intended to limit the scope of this invention in any manner.

I claim:

1. An apparatus for indicating the respiration movements of a patient on a recorder, which comprises:
   (a) a recorder capable of recording an electrical signal;
   (b) two piezoelectric transducers mounted on a support member, wherein said transducers are disposed parallel and opposite to each other; and;
   (c) a belt disposed between said parallel piezoelectric transducers, said belt having at least one portion thereof disposed in a loop-like shape which extends angularly outwardly from the unlooped portion of the belt at an angle of at least 5°, wherein said belt has two ends which form a flexible band adapted to surround a patient's clothing;
   wherein the two piezoelectric transducers generate an electrical signal upon stretching of said flexible band due to respiration movements of said patient, wherein said signal is indicated on said recorder.

2. An apparatus for indicating respiration movements according to claim 1, wherein said belt is situated near one of said transducers, wherein the crest of said loop of said belt faces said transducer.

3. An apparatus for indicating respiration movements according to claim 1, wherein the loop angle is about 20°.

4. An apparatus for indicating respiration movements according to claim 1, wherein the two ends of said belt are joined by a fastener means.

5. An apparatus for indicating respiration movements according to claim 1, wherein said belt is made from polyvinyl chloride, polyamide or polyethylene.

6. An apparatus for indicating respiration movements according to claim 1, wherein only said piezoelectric transducers and the loop portion of said belt are enclosed in a rigid housing from which said end portions of said belt extend.

7. An apparatus for indicating respiration movements according to claim 6, wherein said rigid housing is filled with a resilient material.

8. An apparatus for indicating respiration movements according to claim 7, wherein said resilient material is selected from the group consisting of an elastic glue and silicon rubber.

9. An apparatus for indicating respiration movements according to claim 1, wherein said recorder is an electroencephalograph recorder.

10. An apparatus for indicating respiration movements according to claim 1, wherein said recorder is a strip chart.

11. An apparatus for indicating respiration movements according to claim 1, wherein said loop resembles an inverted U-shaped configuration.

12. An apparatus for indicating respiration movements according to claim 1, wherein said loop resembles a saw-tooth or inverted V-shaped configuration.

13. An apparatus for indicating the respiration movements of a patient on a recorder, which comprises:
   (a) a recorder capable of recording an electrical signal;
   (b) two piezoelectric transducers mounted on a support member, wherein said transducers are disposed parallel to each other; and;
   (c) a belt disposed substantially parallel to one of said piezoelectric transducers, but not disposed between said piezoelectric transducers, said belt having at least one portion thereof disposed in a loop-like shape which extends angularly outwardly from the unlooped portion of the belt at an angle of at least 5°, wherein said belt has two ends which form a flexible band adapted to surround a patient's clothing.

14. An apparatus for indicating respiration movement according to claim 13, wherein the belt is situated near one of said transducers, wherein the crest of said loop faces said transducers.

15. An apparatus for indicating respiration movements according to claim 13, wherein the loop angle is about 20°.

16. An apparatus for indicating respiration movements according to claim 13, wherein the two ends of the belt are joined by fastener means.

17. An apparatus for indicating respiration movements according to claim 13, wherein said belt is made from polyvinyl, polyamide, or polyethylene.

18. An apparatus for indicating respiration movements according to claim 13, wherein only said piezoelectric transducers and the loop portion of said belt are enclosed in a rigid housing from which said end portions of said belt extend.

19. An apparatus for indicating respiration movements according to claim 18, wherein said rigid housing is filled with a resilient material.

20. An apparatus for indicating respiration movements according to claim 19, wherein said resilient material is selected from the group consisting of an elastic glue and silicon rubber.

21. An apparatus for indicating respiration movements according to claim 13, wherein said recorder is an electroencephalograph recorder.

22. An apparatus for indicating respiration movements according to claim 13, wherein said recorder is an strip chart.

23. An apparatus for indicating respiration movements according to claim 13, wherein said loop resembles an inverted U-shaped configuration.

24. An apparatus for indicating respiration movements according to claim 13, wherein said loop resembles a saw-tooth or inverted V-shaped configuration.

* * * * *